US009651550B2

(12) United States Patent
Van Cleve et al.

(10) Patent No.: US 9,651,550 B2
(45) Date of Patent: *May 16, 2017

(54) AUTOMATED IMMUNOANALYZER SYSTEM FOR PERFORMING DIAGNOSTIC ASSAYS FOR AUTOIMMUNE AND INFECTIOUS DISEASES

(71) Applicant: Hycor Biomedical, Inc., Indianapolis, IN (US)

(72) Inventors: Mark David Van Cleve, Long Beach, CA (US); Elaine Grace Taine, Anaheim, CA (US); Douglas John Canfield, Ludington, MI (US); Stephanie TuVi Ortega, Santa Ana, CA (US); Taylor Addison Reid, Carlsbad, CA (US)

(73) Assignee: Hycor Biomedical, LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/673,698

(22) Filed: Mar. 30, 2015

(65) Prior Publication Data

US 2015/0204867 A1    Jul. 23, 2015

Related U.S. Application Data

(63) Continuation-in-part of application No. 14/215,720, filed on Mar. 17, 2014.

(60) Provisional application No. 61/791,295, filed on Mar. 15, 2013, provisional application No. 61/791,879, filed on Mar. 15, 2013.

(51) Int. Cl.

| | | |
|---|---|---|
| *G01N 33/564* | (2006.01) | |
| *G01N 35/10* | (2006.01) | |
| *G01N 21/64* | (2006.01) | |
| *G01N 33/543* | (2006.01) | |
| *G01N 33/68* | (2006.01) | |
| *G01N 33/53* | (2006.01) | |
| *G01N 33/58* | (2006.01) | |
| *G01N 35/00* | (2006.01) | |
| *G01N 21/76* | (2006.01) | |
| *G01N 33/569* | (2006.01) | |
| *G01N 35/04* | (2006.01) | |

(52) U.S. Cl.
CPC ......... *G01N 33/564* (2013.01); *G01N 21/645* (2013.01); *G01N 21/6428* (2013.01); *G01N 21/76* (2013.01); *G01N 33/5306* (2013.01); *G01N 33/54326* (2013.01); *G01N 33/54393* (2013.01); *G01N 33/569* (2013.01); *G01N 33/582* (2013.01); *G01N 33/6854* (2013.01); *G01N 33/6893* (2013.01); *G01N 35/0098* (2013.01); *G01N 35/1011* (2013.01); *G01N 2021/6484* (2013.01); *G01N 2035/0453* (2013.01); *G01N 2035/1062* (2013.01); *G01N 2201/062* (2013.01); *G01N 2201/08* (2013.01); *G01N 2333/4703* (2013.01); *G01N 2333/62* (2013.01); *G01N 2333/78* (2013.01); *G01N 2800/24* (2013.01); *Y10T 436/119163* (2015.01)

(58) Field of Classification Search
CPC ............ G01N 33/564; G01N 21/6428; G01N 21/645; G01N 33/5306; G01N 33/54326; G01N 33/54393; G01N 33/569; G01N 33/582; G01N 33/6854; G01N 33/6893; G01N 35/0098; G01N 35/1011; G01N 2021/6484; G01N 2035/0453; G01N 2035/1062; G01N 2201/062; G01N 2201/08; G01N 2333/4703; G01N 2333/62; G01N 2333/78; G01N 2800/24; Y01Y 436/119163
See application file for complete search history.

(56) References Cited

U.S. PATENT DOCUMENTS 3,628,682 A    12/1971  Paulson
3,729,556 A *   4/1973  Schwarz ................ C07K 16/34
                                                424/173.1

(Continued)

FOREIGN PATENT DOCUMENTS

| CN | 101696973 A | 4/2010 |
| CN | 102478571 A | 5/2012 |

(Continued)

OTHER PUBLICATIONS

Sanchez-Guerrero et al., Utility of Anti-Sm, Anti-Ro/SS-A and Anti-La/SS-b (Extractable Nuclear Antigens) Detected by Enzyme-Linked Immunosorbent Assay for the Diagnosis of Systemic Lupus Erythematosus, Arthritis & Rheumatism, 39(6), 1996, 1055-1061.*

(Continued)

*Primary Examiner* — Andrea S Grossman
(74) *Attorney, Agent, or Firm* — K&L Gates LLP; Louis C. Cullman; Brian J. Novak

(57) ABSTRACT

A quantitative method for diagnosing an autoimmune disease or an infectious disease comprising performing an automated diagnostic assay, comprising: incubating a capture reagent with a streptavidin-coated medium to form a solid phase complex, wherein the capture reagent is a biotinylated autoantigen or infectious disease antigen; washing the solid phase complex to remove excess capture reagent; incubating the solid phase complex with a serum sample to form an immune complex; washing the immune complex to remove any unbound sample; incubating the immune complex with a conjugate to create an immune-conjugate complex; washing the immune-conjugate complex to remove any unbound conjugate; introducing a substrate capable of generating a quantifiable response; and calibrating the response generated from introducing the substrate.

5 Claims, 2 Drawing Sheets

(56) References Cited

U.S. PATENT DOCUMENTS

| | | |
|---|---|---|
| 4,291,230 A | 9/1981 | Heiss |
| 4,778,751 A | 10/1988 | El Shami et al. |
| 4,849,337 A | 7/1989 | Calenoff et al. |
| 5,001,049 A | 3/1991 | Klein et al. |
| 5,395,752 A | 3/1995 | Law et al. |
| 5,395,938 A | 3/1995 | Ramakrishnan |
| 5,468,453 A | 11/1995 | Holt et al. |
| 5,543,332 A | 8/1996 | Lihme et al. |
| 5,583,001 A | 12/1996 | Bobrow et al. |
| 5,643,566 A * | 7/1997 | Hanisch et al. ............ 424/85.4 |
| 5,672,475 A | 9/1997 | Lee et al. |
| 5,674,698 A | 10/1997 | Zarling et al. |
| 5,686,253 A | 11/1997 | Skold et al. |
| 5,690,907 A | 11/1997 | Lanza et al. |
| 5,698,397 A | 12/1997 | Zarling et al. |
| 5,736,353 A | 4/1998 | Weavers et al. |
| 5,770,700 A * | 6/1998 | Webb et al. ............ 530/383 |
| 5,776,487 A | 7/1998 | Maxfield Wilson et al. |
| 5,776,785 A | 7/1998 | Lin et al. |
| 5,804,391 A | 9/1998 | Klemt et al. |
| 5,807,997 A | 9/1998 | Batista |
| 5,879,885 A | 3/1999 | Becker |
| 5,879,888 A | 3/1999 | Aizawa et al. |
| 5,922,558 A | 7/1999 | Akhavan-Tafti |
| 5,942,407 A | 8/1999 | Liotta et al. |
| 5,952,238 A | 9/1999 | Tsuji et al. |
| 5,965,378 A | 10/1999 | Schlieper et al. |
| 5,973,124 A | 10/1999 | Bayer et al. |
| 5,994,519 A | 11/1999 | Osbourn et al. |
| 6,059,561 A | 5/2000 | Becker |
| 6,066,448 A | 5/2000 | Wohlstadter et al. |
| 6,066,462 A | 5/2000 | Goueli |
| 6,068,979 A | 5/2000 | Akhavan-Tafti |
| 6,087,188 A | 7/2000 | Johansen et al. |
| 6,090,545 A | 7/2000 | Wohlstadter et al. |
| 6,103,537 A | 8/2000 | Ullman et al. |
| 6,140,045 A | 10/2000 | Wohlstadter et al. |
| 6,153,442 A | 11/2000 | Pirio et al. |
| 6,159,699 A | 12/2000 | Brown et al. |
| 6,165,800 A | 12/2000 | Jiang et al. |
| 6,180,336 B1 | 1/2001 | Osbourn et al. |
| 6,180,340 B1 | 1/2001 | Nelson |
| 6,235,480 B1 | 5/2001 | Shultz et al. |
| 6,303,325 B1 | 10/2001 | Mehta et al. |
| 6,328,934 B1 | 12/2001 | Ljung et al. |
| 6,342,588 B1 | 1/2002 | Osbourn et al. |
| 6,348,310 B1 | 2/2002 | Goueli |
| 6,350,579 B1 | 2/2002 | Nelson |
| 6,379,909 B1 | 4/2002 | Ipsen et al. |
| 6,399,299 B1 | 6/2002 | Bobrow et al. |
| 6,399,397 B1 | 6/2002 | Zarling et al. |
| 6,432,662 B1 | 8/2002 | Davis et al. |
| 6,489,123 B2 | 12/2002 | Osbourn et al. |
| 6,489,309 B1 | 12/2002 | Singh et al. |
| 6,528,322 B1 | 3/2003 | Carlsson et al. |
| 6,537,829 B1 | 3/2003 | Zarling et al. |
| 6,730,479 B2 | 5/2004 | Shultz et al. |
| 6,733,980 B1 | 5/2004 | Venge et al. |
| 6,737,278 B1 | 5/2004 | Carlsson et al. |
| 6,753,157 B2 | 6/2004 | Goueli |
| 6,777,198 B2 | 8/2004 | Mendel-Hartvig et al. |
| 6,806,058 B2 | 10/2004 | Jesperson et al. |
| 6,812,038 B1 | 11/2004 | Mendel-Hartvig et al. |
| 6,872,828 B2 | 3/2005 | Akhavan-Tafti et al. |
| 6,897,036 B2 | 5/2005 | Akhavan-Tafti et al. |
| 6,902,889 B1 | 6/2005 | Carlsson et al. |
| 6,924,154 B2 | 8/2005 | Evangelista et al. |
| 6,939,681 B1 | 9/2005 | Ipsen et al. |
| 6,949,524 B2 | 9/2005 | Singh et al. |
| 6,958,214 B2 | 10/2005 | Braun |
| 6,972,326 B2 | 12/2005 | Haugland et al. |
| RE39,047 E | 3/2006 | Aizawa et al. |
| 7,018,847 B2 | 3/2006 | Mendel-Hartvig et al. |
| 7,074,622 B2 | 7/2006 | Qiao et al. |
| 7,083,986 B2 | 8/2006 | Natrajan et al. |
| 7,097,995 B2 | 8/2006 | Jiang et al. |
| 7,102,005 B2 | 9/2006 | Agnew et al. |
| 7,183,072 B1 | 2/2007 | Hainfeld |
| 7,183,119 B2 | 2/2007 | Qiao et al. |
| 7,247,726 B2 | 7/2007 | Akhavan-Tafti et al. |
| 7,262,019 B2 | 8/2007 | Kovalenko |
| 7,297,555 B2 | 11/2007 | Evangelista et al. |
| 7,300,655 B2 | 11/2007 | Hansen et al. |
| 7,309,615 B2 | 12/2007 | Natrajan et al. |
| 7,319,041 B2 | 1/2008 | Natrajan et al. |
| 7,364,872 B1 | 4/2008 | Hainfeld |
| 7,381,797 B2 | 6/2008 | Woerner et al. |
| 7,393,638 B2 | 7/2008 | Chou |
| 7,405,084 B1 | 7/2008 | Mendel-Hartvig et al. |
| 7,439,014 B2 * | 10/2008 | Pamula et al. ............ 435/4 |
| 7,445,894 B2 | 11/2008 | Agnew et al. |
| 7,459,284 B2 | 12/2008 | Jiang et al. |
| 7,491,553 B2 | 2/2009 | Brown et al. |
| 7,501,498 B2 | 3/2009 | Hansen et al. |
| 7,514,223 B2 | 4/2009 | Yang et al. |
| 7,521,184 B2 | 4/2009 | Radka et al. |
| 7,521,577 B2 | 4/2009 | Gee et al. |
| 7,556,928 B2 | 7/2009 | Jesperson et al. |
| 7,560,556 B2 | 7/2009 | Akhavan-Tafti et al. |
| 7,563,566 B2 | 7/2009 | Woerner et al. |
| 7,592,153 B2 | 9/2009 | Hainfeld |
| 7,611,909 B1 | 11/2009 | Natrajan et al. |
| 7,674,629 B2 | 3/2010 | Waheed et al. |
| 7,759,133 B2 | 7/2010 | Van Neerven |
| 7,785,904 B2 | 8/2010 | Natrajan et al. |
| 7,799,534 B2 | 9/2010 | Akhavan-Tafti |
| 7,824,928 B2 | 11/2010 | Evangelista et al. |
| 7,833,983 B2 | 11/2010 | Mahler |
| 7,842,475 B2 | 11/2010 | Zheng et al. |
| 7,842,784 B2 | 11/2010 | Nakayama et al. |
| 7,851,184 B2 | 12/2010 | Pollack et al. |
| 7,871,781 B2 | 1/2011 | Rundstrom et al. |
| 7,875,467 B2 | 1/2011 | Natrajan et al. |
| 7,879,575 B2 | 2/2011 | Kricka et al. |
| 7,888,060 B2 | 2/2011 | Hainfeld et al. |
| 7,892,853 B2 | 2/2011 | Brown et al. |
| 7,906,293 B2 | 3/2011 | Mattingly et al. |
| 7,923,214 B2 | 4/2011 | Akhavan-Tafti |
| 7,951,554 B2 | 5/2011 | Hainfeld et al. |
| 7,951,910 B2 | 5/2011 | Schwarz et al. |
| 7,985,557 B2 | 7/2011 | Kosmeder et al. |
| 8,034,631 B2 | 10/2011 | Brown et al. |
| 8,034,632 B2 | 10/2011 | Brown et al. |
| 8,093,066 B2 | 1/2012 | Brown et al. |
| 8,342,736 B2 | 1/2013 | Luotola et al. |
| 8,349,620 B2 | 1/2013 | Brown et al. |
| 9,075,055 B2 | 7/2015 | Diamond et al. |
| 2003/0031685 A1 | 2/2003 | Stumvoll et al. |
| 2003/0042428 A1 | 3/2003 | Peukert et al. |
| 2003/0073121 A1 | 4/2003 | Mendel-Hartvig et al. |
| 2004/0023309 A1 | 2/2004 | Noll |
| 2004/0023412 A1 | 2/2004 | Carlsson et al. |
| 2004/0202577 A1 | 10/2004 | McNeil et al. |
| 2004/0222384 A1 | 11/2004 | Lee et al. |
| 2005/0244828 A1 * | 11/2005 | Kreitman et al. ............ 435/6 |
| 2006/0008895 A1 | 1/2006 | Chen et al. |
| 2006/0127281 A1 | 6/2006 | Bjornson et al. |
| 2006/0252097 A1 | 11/2006 | Deutscher et al. |
| 2007/0161055 A1 | 7/2007 | Corry et al. |
| 2007/0166776 A1 | 7/2007 | Noll |
| 2007/0183978 A1 | 8/2007 | Preuss et al. |
| 2007/0254308 A1 | 11/2007 | Bobrow et al. |
| 2007/0282362 A1 | 12/2007 | Berg et al. |
| 2008/0003142 A1 * | 1/2008 | Link et al. ............ 422/82.08 |
| 2008/0124738 A1 | 5/2008 | Green et al. |
| 2008/0293161 A1 | 11/2008 | Deutscher et al. |
| 2009/0088336 A1 | 4/2009 | Burd et al. |
| 2009/0176201 A1 | 7/2009 | Jablonski et al. |
| 2009/0286258 A1 | 11/2009 | Kaur et al. |
| 2009/0298199 A1 | 12/2009 | Corry et al. |
| 2010/0075374 A1 | 3/2010 | Lim et al. |
| 2010/0190689 A1 | 7/2010 | Thornton et al. |
| 2010/0284583 A1 | 11/2010 | Ljung |
| 2010/0332143 A1 | 12/2010 | Onell et al. |

| | | | |
|---|---|---|---|
| 2011/0076692 A1* | 3/2011 | Sista et al. ............... 435/7.4 | |
| 2011/0151582 A1 | 6/2011 | Basile | |
| 2011/0275095 A1 | 11/2011 | Babson | |
| 2011/0287455 A1 | 11/2011 | Venge | |
| 2012/0264230 A1 | 10/2012 | Brown et al. | |
| 2014/0274784 A1 | 9/2014 | Van Cleve et al. | |
| 2015/0177145 A1 | 6/2015 | Diamond et al. | |
| 2015/0177146 A1 | 6/2015 | Diamond et al. | |
| 2015/0204871 A1 | 7/2015 | Van Cleve et al. | |

FOREIGN PATENT DOCUMENTS

| | | |
|---|---|---|
| EP | 0353592 A2 | 2/1990 |
| EP | 0355849 A2 | 2/1990 |
| EP | 0981043 A1 | 2/2000 |
| EP | 1054250 A1 | 11/2000 |
| EP | 1279946 A2 | 1/2003 |
| EP | 1684060 A1 | 7/2006 |
| WO | 02/076477 A1 | 10/2002 |
| WO | 2007/133710 A2 | 11/2007 |
| WO | 2014/145581 A1 | 9/2014 |
| WO | 2014/145619 A1 | 9/2014 |

OTHER PUBLICATIONS

Sista et al., Heterogeneous immunoassays using magnetic beads on a digital microfluidic platform, Lab on a Chip, 2008, 8, 2188-2196 ("Sista (b)").*

International Application No. PCT/US2015/023408 filed on Mar. 30, 2015.

International Search Report and Written Opinion for PCT/US2014/030373 dated Jul. 30, 2014.

International Search Report and Written Opinion for PCT/US2014/030414 dated Aug. 8, 2014.

International Search Report and Written Opinion for PCT/US2015/023408 dated Jul. 2, 2015.

Levy et al., In vitro methods for diagnosing allergy and directing therapy. US Respiratory Disease, vol. 6, pp. 63-67 (2010).

Nichkova et al., Multiplexed immunoassays for proteins using magnetic luminescent nanoparticles for internal aalibration. Analytical Biochemistry 369:34-40 (2007).

* cited by examiner

AUTOMATED IMMUNOANALYZER SYSTEM FOR PERFORMING DIAGNOSTIC ASSAYS FOR AUTOIMMUNE AND INFECTIOUS DISEASES

CROSS-REFERENCE TO RELATED APPLICATIONS

This application is a continuation-in-part to U.S. patent application Ser. No. 14/215,720, filed Mar. 17, 2014, which is related to and claims priority to U.S. Provisional Patent Applications 61/791,295 and 61/791,879, each of which were filed on Mar. 15, 2013, the complete and entire disclosures of all of which are hereby expressly incorporated by reference.

TECHNICAL FIELD

The present teachings are related to a system and process for performing diagnostic assays, and more particularly to an automated immunoanalyzer system and process for performing diagnostic assays for infectious and autoimmune diseases.

SUMMARY OF THE DISCLOSURE

In accordance with certain aspects of the present application, a quantitative method for performing an automated diagnostic assay for autoimmune or infectious diseases is provided and comprises the steps of incubating a capture reagent with a streptavidin-coated medium to form a solid phase complex, wherein the capture reagent is a biotinylated autoantigen or infectious disease antigen; washing the solid phase complex to remove excess capture reagent; incubating the solid phase complex with a serum sample to form an immune complex; washing the immune complex to remove any unbound sample; incubating the immune complex with a conjugate to create an immune-conjugate complex; washing the immune-conjugate complex to remove any unbound conjugate; introducing a substrate capable of generating a quantifiable response; and calibrating the response generated from the substrate.

In accordance with yet other aspects of the present application, a controlled process for binding fluorescent labels to particles within a patient sample is provided. In accordance with this aspect of the present disclosure, the process includes binding luminescent labels to the particles, and quantifying the particles remaining after a series of washing steps in order to normalize a luminescence signal from the patient sample. According to this illustrative process, the luminescent labels are bound to the particles in proportion to a number of bound analyte molecules.

In accordance with still other aspects of the present disclosure, quantitative methods for evaluating autoimmune-specific immunoglobulins in a serum sample designed for use on an automated platform are provided. In accordance with this method, biotinylated capture reagent is incubated with a streptavidin-coated solid phase to illicit adhesion of the capture reagent to the solid phase by exploitation of the biotin-streptavidin interaction. The capture-reagent solid phase complex is then washed to remove excess biotinylation capture reagent. A serum sample is then incubated with the capture-reagent solid phase complex to illicit binding of autoantigen-specific immunoglobulins (IgG, IgM, or IgA) present in the serum to the presented capture reagent and to create an immune complex. The immune complex is then washed to remove unbound immunoglobulin and then incubated with labeled anti-immunoglobulin conjugates to illicit binding of the conjugate to the autoantigen-specific immunoglobulin component of the immune complex and to create an immune-conjugate complex. The immune-conjugate complex is washed to remove the unbound labeled anti-immunoglobulin and then a substrate capable of generating a quantifiable response is introduced. The quantifiable response generated from adding the substrate is calibrated and the reported value adjusted for bead retention.

In accordance with still other aspects of the present disclosure, quantitative methods for evaluating infectious agent-specific immunoglobulins in a serum sample designed for use on an automated platform is provided. In accordance with this method, biotinylated capture reagent is incubated with a streptavidin-coated solid phase to illicit adhesion of the capture reagent to the solid phase by exploitation of the biotin-streptavidin interaction. The capture-reagent solid phase complex is then washed to remove excess biotinylation capture reagent. A serum sample is then incubated with the capture-reagent solid phase complex to illicit binding of infectious agent-specific immunoglobulins (IgG, IgM, or IgA) present in the serum to the presented capture reagent and to create an immune complex. The immune complex is then washed to remove unbound immunoglobulin and then incubated with labeled anti-immunoglobulin conjugates to illicit binding of the conjugate to the autoantigen-specific immunoglobulin component of the immune complex and to create an immune-conjugate complex. The immune-conjugate complex is washed to remove the unbound labeled anti-immunoglobulin and then a substrate capable of generating a quantifiable response is introduced. The quantifiable response generated from adding the substrate is calibrated and the reported value adjusted for bead retention.

In accordance with certain aspects herein, the biotinylated capture reagent is a biotinylated autoantigen or a biotinylated infectious agent.

In accordance with certain aspects herein, the biotinylated capture reagent is derived from the biotinylation of a purified protein, enzyme, or antibody.

In accordance with other aspects herein, the biotinylated capture reagent is derived from the biotinylation of an infectious agent extract comprised of a multiplicity of antigens.

According to specific illustrative aspects of the present disclosure, the biotinylated capture reagent exists as an amalgam of multiple biotinylated capture reagents of different origins including purified proteins, enzymes, antibodies and extracts.

According to yet another specific illustrative aspect of the present disclosure, the streptavidin-coated solid phase is a universal fluorescent-labeled magnetic microparticle.

In accordance with certain aspects of the present disclosure, one or more of the washing steps include washing the solid phase complexes by magnetically sequestering the complex within a confined area of a reaction cuvette.

In accordance with yet other illustrative aspects of the present disclosure, the step of incubating the capture reagent-solid phase complex with a serum sample includes incubating a capture reagent-solid phase complex that is retained in a suspension by a reaction diluent including a high concentration of human serum albumin (HSA).

In accordance with still another illustrative aspect of the present disclosure, the step of incubating the immune complex with a labeled anti-immunoglobulin conjugate comprises incubating an immune complex that is retained in a suspension by a conjugate diluent including a nominal concentration of polyethylene glycol.

According to certain specific aspects of the present disclosure, horseradish peroxidase (HRP) conjugated to an anti-immunoglobulin antibody can be used as an indirect label when washing the immune complex to remove unbound immunoglobulin, particularly as the reaction of PS-ATTO® (a substrate for the chemiluminescent detection of HRP conjugates, Lumigen, Inc. Corp., Southfield, Mich.) with an HRP labeled conjugate generates sustained high-intensity luminescence for maximum detection sensitivity in solution assays.

According to still other specific aspects of the present disclosure, the addition of a substrate to the immune-conjugate complex comprises adding LUMIGEN® (Lumigen, Inc., Southfield, Mich.) PS-ATTO® as the substrate capable of generating a quantifiable response, the quantifiable response existing as a chemiluminescent signal generated by HRP PS-ATTO® reporter system and detected by a luminometer within an optics box.

In accordance with certain aspects of the present teachings, the step of adjusting a quantifiable response for bead retention includes the steps of: transferring the substrate and immune-conjugate complex to an optics box wherein both fluorescent and chemiluminescent signals are quantified; employing a ratio of initial to final fluorescence to adjust the quantified chemiluminescent signal for bead retention; and calibrating the adjusted chemiluminescent signal to calculate a reported value. To transfer the substrate and immune-conjugate complex to the optics box, an automated pipette arm with a reusable pipette tip aspirating the sample can be utilized. Within the optics box, fluorescence is measured to determine bead retention, and luminescence is measured to detect the RLU signal generated by the chemistry. The measurements are entered into an algorithm to generate a "bead retention adjusted RLU" that is compared the calibration curve RLU, thereafter an immunoglobulin concentration is assigned.

Still other objects and benefits of the invention will become apparent from the following written description along with the accompanying figures.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure taken in conjunction with the accompanying drawings, wherein.

Figure 1:
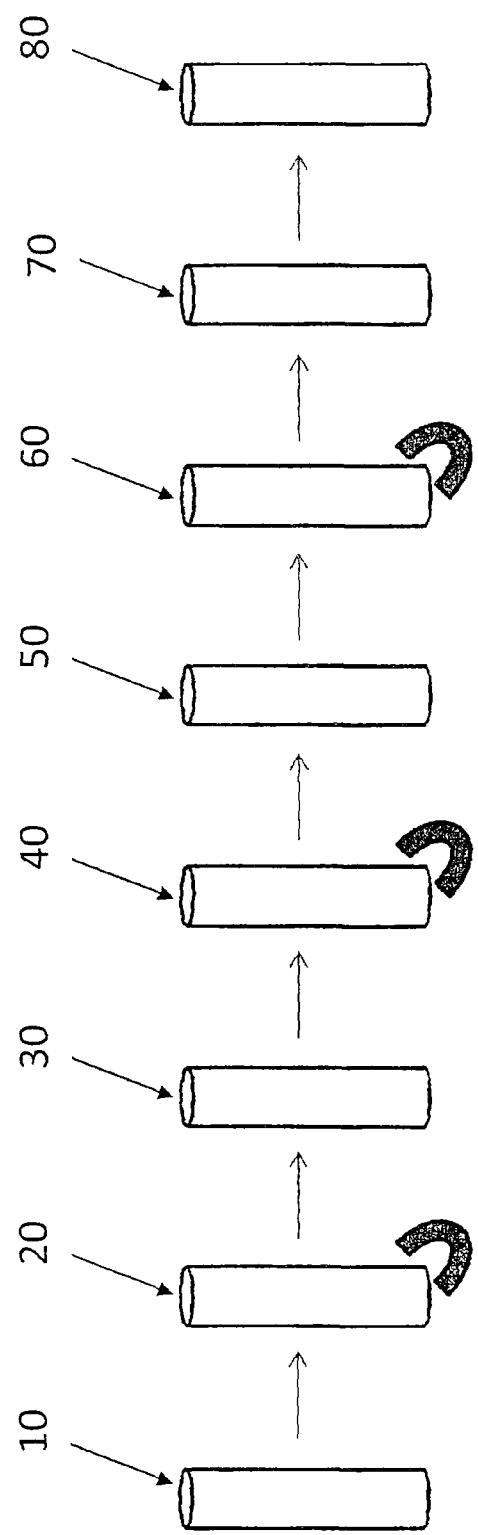
FIG. 1 is a schematic illustration of a method for performing an automated diagnostic assay in accordance with the present application.

Corresponding reference characters indicate corresponding parts throughout the several views. Although the exemplification set out herein illustrates embodiments of the disclosure, in several forms, the embodiments disclosed below are not intended to be exhaustive or to be construed as limiting the scope of the disclosure to the precise forms disclosed.

DETAILED DESCRIPTION

Disclosed herein is an automated immunoanalyzer instrument, reagent system, and methods for performing diagnostic assays for infectious and autoimmune diseases.

Before describing in detail the illustrative automated immunoanalyzer system and method of the present disclosure, it should be understood and appreciated herein that as a way of minimizing background signals from excess or unbound materials, immunoassays generally require that one or more separation phases be carried out in the reaction cuvette. To facilitate the separation or washing process, a variety of techniques can be used, including, but not limited to, well coating techniques, bead coating techniques, or the use of paramagnetic particles. Each of these separation media are coated with a capture reagent that will bind analyte molecules of interest in the patient's blood sample. In accordance with certain aspects of the present teachings, the biotinylated capture reagent can exist as an amalgam or mixture (i.e., capture reagents from a similar category but from different genus species). As those of skill in the art would understand and appreciated herein, numerous capture reagents are available and can be used in accordance with the present teachings. It should be understood herein that the amount and volume of each of the individual capture reagents used in accordance with the present teachings depends on their potency (i.e. their ability to produce a detectable response).

When paramagnetic particles are used as the separation media, the paramagnetic particles are pulled to the wall of the cuvette by magnets during the washing process and then all of the liquid is aspirated. As those of skill in the art will understand and appreciate herein, during conventional washing processes, some of the paramagnetic particles may be aspirated along with the liquid and will therefore be lost for further chemistry processing. The loss of the magnetic particles becomes even more significant if the immunoassay procedure involves several wash steps.

One of the objectives of the present teachings is to take into account the loss of paramagnetic particles that occur on an immunochemistry analyzer during these washing processes. To accomplish this, in accordance with certain aspects of the present teachings, the analytes of interest in a patient's blood sample bind to a capture reagent that has in turn been bound to the surface of a paramagnetic particle. Luminescent labels are then bound to these analyte molecules. When a luminescing reagent or substrate is added to the cuvette it reacts with the luminescent label to produce light that is detectable by the analyzer's optical detector. In addition, if the paramagnetic particles have a fluorescent label attached, fluorescently reading the contents within the cuvette will provide a means for determining the fraction of the particles that were lost during the wash steps.

According to certain aspects of the present disclosure, the automated analyzer utilizes common paramagnetic particles for the assays, including, but not limited to, magnetic beads or microparticles. For each assay onboard the analyzer, a capture reagent is incubated and bound to the universal particles in a reaction cuvette to produce an assay-specific, particle-based reagent, sometimes referring to herein as a capture-reagent solid phase complex. In accordance with certain aspects of the present disclosure, a capture reagent that can be used for performing a diagnostic immunoassay is comprised of biotin-antigen, 10 mM sodium phosphate, pH 7.4, 0.9% NaCl, 0.05% Tween-20, 1% (w/v) human serum albumin, 1% (v/v) ProClin 950, up to 5% (v/v) glycerol. In accordance with still other aspects of the present disclosure, another capture reagent that can be used for performing a diagnostic immunoassay is comprised of biotin-antigen, 10 mM sodium phosphate, pH 7.4, 0.9% (w/v) NaCl, 0.05% Tween-20, 1% (w/v) bovine serum albumin, 1% (v/v) ProClin 950, 1% protease inhibitor cocktail, 0.1 mM DTT, 25% (up to 30%) (v/v) glycerol.

After undergoing a washing process, the patient sample, and optionally a diluent if needed, is added to the particles in the cuvettes and incubated. This results in the capture of specific analyte molecules in the patient's blood sample. In accordance with one specific illustrative aspect of the present disclosure, the reaction diluent (sample diluent) is comprised of 10 mM sodium phosphate, pH 7.4, 500 mM NaCl, 0.02% Tween-20, 1% (w/v) human serum albumin, 1% (v/v) human IgG, 1% (v/v) ProClin 950, 0.005% Antifoam-B v/v, 2% (w/v) PEG 6,000. In accordance with yet another specific illustrative aspect of the present disclosure, the reaction diluent (sample diluent) is comprised of 10 mM sodium phosphate, pH 7.4, 500 mM NaCl, 0.02% Tween-20, 25% (w/v) human serum albumin, 1% (v/v) ProClin 950.

In accordance with these illustrative embodiments, it should be understood herein that the high percentage of HSA (25%) functions in part to increase the viscosity of the reaction medium in order to retain beads in suspension during the incubation step. In addition, high HSA also reduces non-specific binding during this incubation, and improves relative light unit (RLU) linearity upon dilution of the patient sample.

Another washing process is then performed to remove any excess or unbound sample, and then a luminescent label and a conjugate is added to the cuvette. When added to the cuvette, it can be expected that some portion of the conjugate will bind to the capture reagent/sample complex on the paramagnetic particles after an incubation period. The particles then undergo another wash process to remove any unbound conjugate, and then the substrate is added to the cuvette and incubated for a short period of time to allow the chemiluminescent glow reaction to reach equilibrium.

After equilibrium is reached, luminescence and fluorescence readings of the sample are taken. Since the paramagnetic particles are contained on the analyzer in a common reagent vial and are maintained in a state of uniform suspension before being pipetted into the reaction cuvettes, initial fluorescence measurements of the particles after they are pipetted into the cuvettes, when combined with the final fluorescence measurement for each test, can be used to determine the fraction of the initial particles that remain in the cuvette after the immunoassay process. The fraction remaining is given by the following formula:

$$\text{Particle fraction remaining} = \frac{F_{final} - F_{background}}{F_{initial} - F_{background}},$$

where F represents the corrected fluorescent signal (i.e., the measured signal corrected by the counting efficiency of the optical detector). Because the optical detector has a certain time resolution, as the number of photons detected per unit time increases, the likelihood of two photons arriving at the detector within that time resolution also increases. Since these two photons cannot be resolved by the detector, they will count as a single photon. Thus, the detection efficiency of the optical detector decreases as the incident photon flux increases.

Because of the very high flux of fluorescence excitation photons which interact with and scatter from the container walls for the paramagnetic particles, there will be a certain number of photons that will be counted by the optical detector, even when no fluorescent material is present. This corrected background signal is represented by $F_{background}$.

The use of a fluorescent measurement to determine the percentage of the initial paramagnetic particles that remain in a reaction cuvette throughout the immunoassay process is beneficial because the process does not limit system throughput, particularly because the process does not restrict the timing or parallel processing that can be achieved. Most conventional immunoassay analyzers, on the other hand, rely on very reproducible processing of paramagnetic particles and samples, which do indeed restrict the timing or parallel processing that can be achieved, and as a result, also limit system throughput. While changes in processing efficiency over time in these conventional immunoassay analyzers may go undetected, these changes can be detected with fluorescence detection. The teachings of the present disclosure permit the use of parallel processing (e.g. multiple wash arms), which vary in wash efficiency due to minor mechanical alignment or fluidic differences. Fluorescence readings taken after each step of an immunoassay process are useful for verifying the equivalent functionality of the parallel processes.

An automated immunoanalyzer instrument and reagent system for performing diagnostic assays for infectious and autoimmune diseases in accordance with the above-described methods and techniques is now described in greater detail. As this process is described, it should be understood and appreciated herein that the disclosed instrumentation used to perform the assay can be configured to accept standard or universal collection tubes so that a variety of different tests can be conducted by the system. Those of skill in the art will also understand and appreciate herein that there are many known methods for isolating antigens, including infectious disease and autoimmune antigens from source materials. Because these isolating methods are widely known and accepted within the art, they are not discussed in detail herein, particularly as those of skill in the art will recognize that any acceptable antigen isolation methods may be incorporated into the inventive system without departing from its spirit or scope. After the infectious disease or autoimmune antigens have been isolated, they can then be conjugated with biotin to create biotinylated antigens or capture reagents. The biotinylated antigens are then contacted with a streptavidin-linked solid support or membrane. In accordance with certain aspects of the present disclosure, the biotinylated capture reagents can be derived from components including, but not necessarily limited to, purified proteins, enzymes, antibodies, DNA, nuclear extracts, cellular extracts and non-protein antigens (e.g., drugs or materials cross-linked to a protein).

As those of skill in the art will understand and appreciate herein, standard biotinylation processes and techniques commonly used for diagnostic infectious and autoimmune disease immunoassays can be utilized in accordance with the present teachings; however the biotin/protein ratio for the reaction can be optimized as needed to ensure optimum performance of the multiple biotinylated reagents used in the chemistry. In accordance with certain aspects of the present teachings, a specific size linker arm of the biotin reagent is NHS-PEG$_{12}$-Biotin. Moreover, for non-protein antigens, the material can be crosslinked to a biotinylated protein for coating onto the streptavidin bead solid phase, while for autoimmune antigens, such as DNA, biotinylated dideoxynucleotides can be incorporated into the DNA.

A schematic illustration of an automated diagnostic assay process in accordance with certain aspects of the present disclosure is shown in FIG. 1. In accordance with this illustrative embodiment, magnetic beads or microparticles manufactured with a streptavidin coating are mixed (incubated) with a known biotinylated antigen (step 10). As those of skill in the art will understand and appreciate herein, the well-known affinity binding between streptavidin and biotin facilitates antigen coating onto the surface of the beads and thereby allows for the use of a universal bead with on-board reagent preparation. It should also be understood and appreciated herein that the amount of time and associated laboratory conditions required in order to incubate the biotinylated capture reagents with the streptavidin-coated solid phase in accordance with the present teachings may vary in light of the specific experiment being conducted, however, in accordance with certain aspects of the present disclosure, a particularly useful incubation time range is from about 1 minute to about 15 minutes, more particularly from about 5 minutes to about 10 minutes and at a temperature of from about 2° C. to about 40° C., more particularly from about 36.8° C. to about 37.2° C.

As shown in Table 1 below, in accordance with this aspect of the present disclosure, the following beads may be used for the magnetic supports disclosed herein:

TABLE 1

| Bead | 1 | 2 | 3 |
|---|---|---|---|
| Vendor | Thermo Scientific | B: Bangs Lab | Pierce |
| Product | SA-Coated Magnetic Bead | BioMag Plus Streptavidin (Cat # BP628) | SA-Coated Magnetic Bead |
| Mean Diameter | 1 μm | ~1.5 μm | 1 μm |
| Size Distribution (Within Lot CV) | ±10% | CV: 30% (1.242 ± 0.402) | NA |
| Biotin Binding Capacity (per mg Bead) | 4 nmol Biotin | >2 μg Biotin (8-26 μg) (Biotin-ALP) | 3.5 nmol Biotin fluorescein |

While numerous processes can be utilized for mixing or incubating the biotinylated antigens with the streptavidin coated beads, in accordance with certain specific embodiments, the products are mixed in a reaction cuvette so that the antigens coat the beads due to the biotin/streptavidin interaction. According to one illustrative embodiment, 10 μL of streptavidin (SA)-coated bead is dispensed into the reaction cuvette, followed by 40 μL biotinylated antigen, which is mixed during dispensation. The mixture is incubated for 1-15 minutes. Excess biotinylated antigen can then be washed off by pulling the magnetic beads to one side of the reaction cuvette and immobilizing them while buffer is washed through the reaction cuvette (step 20). In accordance with one illustrative embodiment, the buffer can be comprised of 10 mM sodium phosphate, pH 7.4, 0.9% (w/v) NaCl, 0.05% (v/v) Tween-20, 10 mg/mL HSA and 1% (v/v) ProClin 950. While those of skill in the art can utilize any readily available immobilization techniques known within the art to cause the magnetic beads to stay on one side of the reaction cuvette, in accordance with certain specific illustrative embodiments, an external magnet is used to immobilize the magnetic beads while the washing step is performed.

The streptavidin coated magnetic beads are then released from the magnetic field and allowed to move freely within the reaction cuvette. A biological sample (serum or plasma) is then added to the reaction cuvette, followed by 40 μL reaction buffer, thereby re-suspending the magnetic beads (step 30). In addition to the biological sample, in accordance with certain aspects of the present disclosure, a high concentration of human serum albumin (HSA) is also used within the suspension to promote macromolecular binding, as well as to keep the magnetic beads within the solution. Human IgG is added into the buffer to keep the reaction linear.

If the sample contains any antibodies (e.g., IgE, IgG, IgM, IgA) that are reactive to any of the antigen bead coatings, such antibodies will bind during this sample incubation step. The sample incubation is kept at 37° C. for 40 minutes. After any antibodies within the patient sample bind with the beads, a second washing step is then performed to remove any non-bound patient sample (step 40). 150 μL of wash buffer concentrate (50 mM sodium phosphate, pH 7.4, 4.5% (w/v) NaCl, 0.05% Tween-20, 0.05% (v/v) ProClin 950, 0.02% (v/v) Antifoam-C v/v) is added to resuspend the bead and then the beads are pulled down with a magnet for 1.5 min. After the solution is removed, the magnet is moved away, and 200 μL of wash buffer is added to resuspend the bead. The wash is then repeated one more time.

After the second washing step is performed, the beads are re-suspended in an antibody that is specific for human immunoglobulin G, M, E, or A (IgG/M/E/A). In accordance with certain aspects of the present disclosure, the antibody is conjugated to an enzyme (such as horseradish peroxidase) to bind to any specific patient antibodies that have been captured by the beads (step 50). The beads are then washed once again to remove any excess antibody (step 60), and a highly sensitive light-forming reagent (e.g., chemiluminescent substrate) is added to maximize detection sensitivity (step 70). Illustrative reagents that can be used as the chemiluminescent substrate in accordance with the teachings of the present disclosure include, but are not limited to, LUMIGEN® PS-ATTO®, SUPERSIGNAL® (chemiluminescent substrate optimized to generate an intense light signal and provide exceptional performance in luminometer-based assays, Pierce Biotechnology, Inc. Rockford, Ill.) ELISA Pico Chemiluminescent Substrate or SUPERSIGNAL® ELISA Femto Maximum Sensitivity Substrate. Those of skill in the art will understand and appreciate that numerous compounds of various structural classes, including xanthene dyes, aromatic amines and heterocyclic amines can be used to produce chemiluminescence under these conditions. These compounds are well-known within the patent literatures and are readily available through many commercial venders. Some non-limiting chemiluminescent compounds include, but are not limited to, dioxetane type molecules, luciferin, LUMIGEN® PS-2, LUMIGEN® PS-3, LUMIGEN® TMA-6, LUMIGEN® TMA-3.

Once the highly sensitive light-forming reagent is added to the reaction cuvette, light is produced (step 80). In accordance with certain embodiments, this light can be measured, by transferring the solution in a pipette tip into a reading station to read both the luminescent signal and fluorescent signal. It should be understood, however, that light emitted in accordance with the present disclosure can be detected by any suitable known detection means available within the art, including, but not limited to, a luminometer, x-ray film, high speed photographic film, a CCD camera, a scintillation counter, a chemical actinometer or visually. As those of skill in the art readily understand and appreciate, each detection means has a different spectral sensitivity, as such; the chosen detection device can be governed by several factors including, the application and use, cost and convenience. Moreover, as used herein, a quantifiable or detectable response that can be measured in accordance with the present disclosure implies that a positive sample with antigen-specific immunoglobulin (Ig, e.g., IgE, IgG, IgM, IgA) caused binding of Anti-Ig-HRP which would generate luminosity (i.e., RLU=relative light unit) upon addition of the substrate. In addition, it should also be understood herein that a quantifiable or detectable response can also apply to a quantifiable response generated by a negative sample.

In accordance with certain aspects of the present teachings, RLU generated by a positive/negative sample for any antigen-specific Ig (sIg) is compared to RLU generated by a total IgE (tIg) calibration curve. The calibration curve is generated by subjecting a range of pre-diluted total Ig (tIg) calibrators (which are generated from WHO standards) evaluated using a biotinylated anti-Ig capture reagent.

Figure 2:
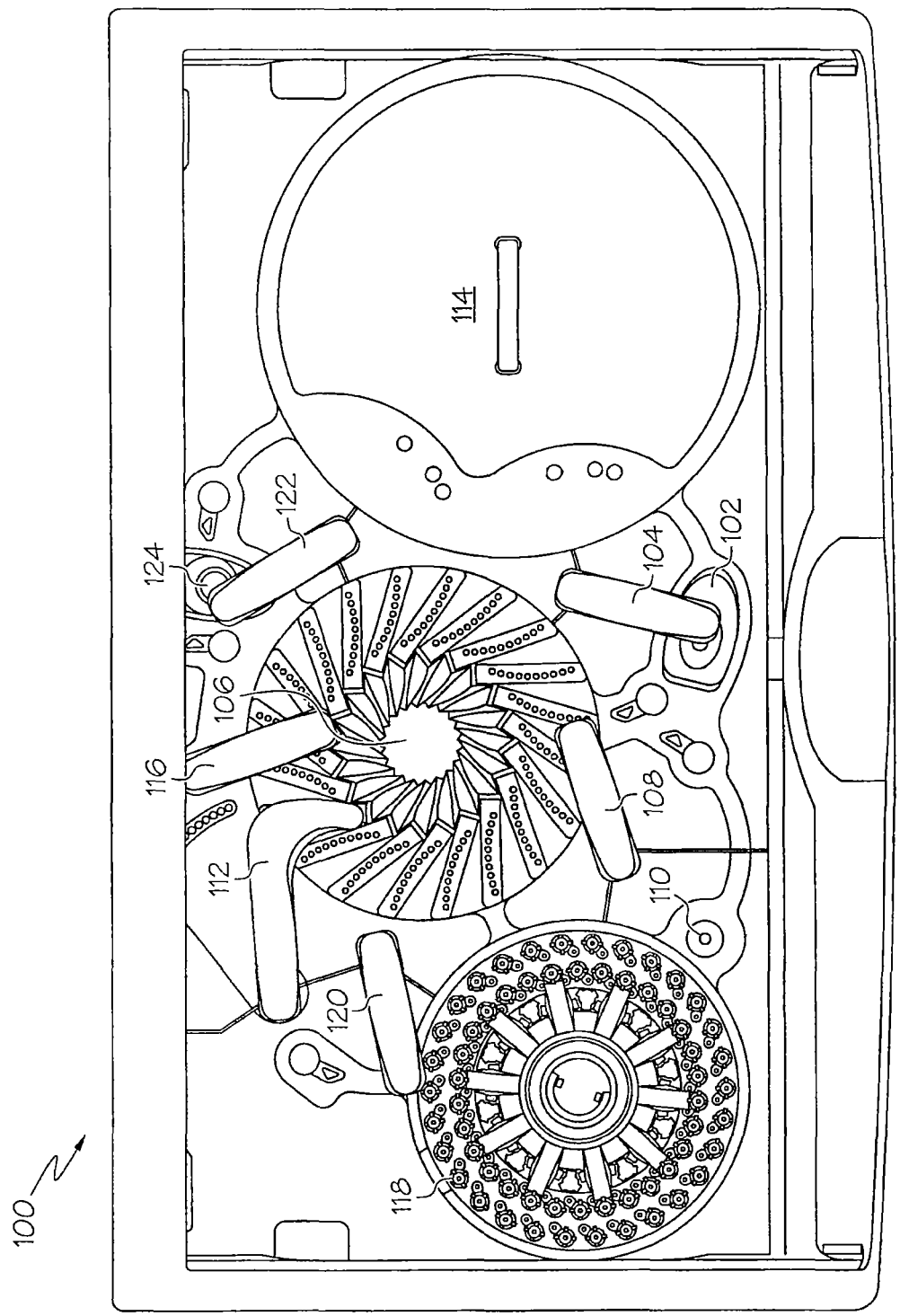
FIG. 2 is a top schematic view of an automated immunochemistry analyzer and reagent system in accordance with the teachings of the present application.

To better understand the mechanical aspects of this disclosure, FIG. 2 illustrates an automated immunochemistry analyzer and reagent system 100 that can be used to quantify and normalize the luminescence signal of an analyte sample in accordance with the teachings of the present disclosure. According to this illustrative aspect, the automated immunochemistry analyzer 100 begins by first dispensing fluorescently labelled paramagnetic particles, or fluo-beads, into a cuvette located within the reaction rotor 106. In accordance with one embodiment herein, an exemplary Fluo-Bead includes Fluo-Bead (SA-Speed Bead, Atto 590 labeled), 1 mg/mL.

The fluo-beads may initially be located in the vortexer 102 and be transferred to the reaction rotor 106 by the R1 pipettor 104. The R1 pipettor 104 can aspirate a desired quantity of the fluo-bead mixture and transfer the aspirated quantity to the reaction rotor 106 where it is injected into the cuvette of the reaction rotor 106. Following the injection into the cuvette, the optics pipettor 108 may aspirate a test sample from the cuvette of the reaction rotor 106 and transfer the test sample to the optics box 110. Once the sample is disposed within the optics box 110, fluorescence and luminescence measurements can be recorded. The initial recording of the fluorescence and luminescence signal can be used as a baseline measurement for the fluorescence signal that can correspond to the initial concentration of fluo-beads in a sample. After recording the measurements, the multi rinse pipettor 112 can rinse the cuvettes using a wash buffer.

Next, fluo-beads may be transferred from the vortexer 102 to a cuvette in the reaction rotor 106 via the R1 pipettor 104. Then, the R1 pipettor 104 may aspirate a capture reagent from the reagent rotor 114 and inject the capture reagent into the cuvette located in the reaction rotor 106. After an incubation period, the single rinse pipettor 116 may inject a rinse buffer to resuspend the fluo-bead. A substantial amount of the suspended fluo-bead may then be localized by magnets within the reaction rotor 106 over a period of time. After the magnets have substantially localized the fluo-beads within the cuvette, the multi rinse pipettor 112 may aspirate and dispose of a portion of the rinse buffer, leaving a portion of the fluo-beads localized within the cuvette. The multi rinse pipettor 112 may proceed to inject a wash buffer into the cuvette of the reaction rotor 106, resuspending the fluo-beads. The fluo-beads may again be localized by the magnets within the reaction rotor 106 to be followed by the multi rinse pipettor 112 aspirating and discarding a portion of the sample that was not localized from the cuvette in the reaction rotor 106.

A patient sample may be contained in a sample tube on in the sample rotor 118. The patient sample may further be partially diluted with a sample diluent. At this point, the sample pipettor 120 may aspirate a portion of the patient sample and inject the patient sample into the cuvette of the reaction rotor 106 to resuspend the fluo-beads. The cuvette containing the patient sample within the reaction rotor 106 may then incubate at a specific temperature, for a specific amount of time. After incubation, the single rinse pipettor 116 may inject the rinse buffer to again resuspend the fluo-beads. Another localization process is performed by the reaction rotor 106 by allowing the fluo-beads to substantially collect within the cuvette near the magnets in the reaction rotor 106. After the localization of the fluo-beads, the multi rinse pipettor 112 may aspirate and discard a portion of the fluid within the cuvette of the reaction rotor 106 that was not localized during the localization process.

A couple of rinse cycles may then be performed on the sample within the cuvette of the reaction rotor 106. The rinse cycle may comprise using the multi rinse pipettor 112 to inject a wash buffer into the cuvette to resuspend the fluo-beads. Another localization step may allow the fluo-beads to collect within the cuvette by the magnets within the reaction rotor 106. After a period allowing for adequate localization of the fluo-beads, the multi rinse pipettor 112 may aspirate and unintentionally discard a portion of the sample, leaving a portion of the fluo-beads within the cuvette of the reaction rotor 106. Another rinse cycle may then occur by using the multi rinse pipettor 112 to again inject wash buffer into the cuvette and allow the fluo-beads to resuspend. Another fluo-bead localization process may utilize the magnets within the reaction rotor 106 to localize the fluo-beads from the rest of the sample. Finally, the multi rinse pipettor 112 may aspirate a portion of the sample that was not localized by the localization process.

At this point, the R2 pipettor 122 may aspirate a conjugate contained in a conjugate cuvette within the reagent rotor 114. The R2 pipettor 122 may then inject the previously aspirated conjugate into the cuvette of the reaction rotor 106. After incubating the cuvette under controlled time and temperature in the reaction rotor 106, the single rinse pipettor 116 may inject a rinse buffer into the cuvette in the reaction rotor 106. Another fluo-bead localization cycle may be performed by allowing magnets within the reaction rotor 106 to substantially localize the fluo-beads within the cuvette. The multi rinse pipettor 112 may aspirate and discard a portion of the sample within the cuvette that has not been localized during the localization cycle.

Two more rinse cycles may be performed on the sample within the cuvette of the reaction rotor 106. The multi rinse pipettor 112 may inject a wash buffer to resuspend the fluo-beads within the cuvette. Another fluo-bead localization cycle may localize the fluo-beads by locating the cuvette within close proximity to the magnets in the reaction rotor 106 over an adequate period of time. After the localization cycle, the multi rinse pipettor 112 may aspirate and discard a portion of the sample that was not localized during the localization cycle. A second wash cycle may then occur by using the multi rinse pipettor 112 to inject the wash buffer to resuspend the fluo-beads. Another localization cycle may utilize the magnets within the reaction rotor 106 to localize the fluo-beads within the cuvette. After the localization process, the multi rinse pipettor 112 may again aspirate and discard a portion of the sample that was not localized during the localization cycle.

At this point, the R2 pipettor 122 may aspirate a portion of conjugate from the reagent rotor 114 and inject the conjugate into the mixed substrate container 124 creating a mixed substrate sample. The R2 pipettor may then aspirate the mixed substrate sample from the mixed substrate container 124 and inject the mixed substrate sample into the cuvette of the reaction rotor 106, resuspending the fluo-bead with the mixed substrate sample. The sample in the cuvette of the reaction rotor 106 may then be aspirated by the optics pipettor 108 and placed in the optics box 110. After the optics box makes fluorescence and luminescence optical observations, the sample is discarded and the multi rinse pipettor rinses the cuvettes of the reaction rotor 106 in preparation for the next test.

Antigens can be proteins, polypeptides, peptides, nucleic acids, lipids, enzymes, immunoglobulins, or nucleotides. As used herein, the term "protein" refers to amino acid sequences longer than 100 amino acids. As used herein, the term "polypeptides" refers to amino acid sequences between 10 and 100 amino acids in length. As used herein, the term "peptides" refers to amino acid sequences less than 10 amino acids in length. As used herein, a "nucleotide" refers to a single purine or pyrimidine molecule while the term "nucleic acid" refers to a nucleotide sequence. For example, DNA is a nucleic acid while guanine is a nucleotide.

Also disclosed herein are quantitative methods for performing an automated diagnostic assay for detection of autoantigen-specific antibodies in a serum sample from a subject for the diagnosis of an autoimmune disease.

Non-limiting examples of autoimmune disorders that can be diagnosed using the method disclosed herein include acute disseminated encephalomyelitis (ADEM), Addison's disease, an anti-phospholipid antibody syndrome (APS), arthritis (e.g., monoarthritis, oligoarthritis, or a polyarthritis like osteoarthritis, rheumatoid arthritis, juvenile idiopathic arthritis, septic arthritis) spondyloarthropathy, autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, a gastro-intestinal disorder (e.g., irritable bowel disease or an inflammatory bowel disease like Crohn's disease or ulcerative colitis), Goodpasture's syndrome, Graves' disease, Guillain-Barré syndrome (GBS), Hashimoto's thyroiditis, hidradenitis suppurativa, idiopathic thrombocytopenic purpura, interstitial cystitis, lupus (e.g., discoid lupus erythematosus, drug-induced lupus erythematosus, lupus nephritis, neonatal lupus, subacute cutaneous lupus erythematosus, systemic lupus erythematosus), morphea, multiple sclerosis (MS), myasthenia gravis, myopathy (e.g., dermatomyositis, inclusion body myositis, polymyositis, myositis), neuromyotonia, Parkinson's disease, pemphigus vulgaris, pernicious anaemia, primary biliary cirrhosis, psoriasis, recurrent disseminated encephalomyelitis, rheumatic fever, schizophrenia, scleroderma, Sjögren's syndrome, a skin disorder (e.g., dermatitis, eczema, statis dermatitis, hidradenitis suppurativa, psoriasis, rosacea or a scleroderma), tenosynovitis, uveitis, vasculitis (e.g., Buerger's disease, cerebral vasculitis, Churg-Strauss arteritis, cryoglobulinemia, essential cryoglobulinemic vasculitis, giant cell arteritis, Golfer's vasculitis, Henoch-Schonlein purpura, hypersensitivity vasculitis, Kawasaki disease, microscopic polyarteritis/polyangiitis, polyarteritis nodosa, polymyalgia rheumatica (PMR), rheumatoid vasculitis, Takayasu arteritis, Wegener's granulomatosis), or vitiligo.

Non-limiting examples of autoantigens include, but are not limited to, aggrecan, alanyl-tRNA syntetase (PL-12), alpha beta crystallin, alpha fodrin (Sptan 1), alpha-actinin, α1 antichymotrypsin, α1 antitripsin, α1 microglobulin, alsolase, aminoacyl-tRNA synthetase, amyloid (e.g., amyloid beta, amyloid P), annexins (e.g., annexin II, annexin V), apolipoproteins (e.g., ApoB, ApoE, ApoE4, ApoJ), aquaporin (e.g., AQP1, AQP2, AQP3, AQP4), bactericidal/permeability-increasing protein (BPI), β-globin precursor BP1, β-actin, β-lactoglobulin A, β2-glycoprotein I, β2-microglobulin, blood group antigens (e.g., Rh blood group antigens, I blood group antigens, ABO blood group antigens), C reactive protein (CRP), calmodulin, calreticulin, cardiolipin, catalase, cathepsin B, centromere proteins (e.g., CENP-A, CENP-B), chondroitin sulfate, chromatin, collagen (e.g., types I, II, III, IV, V, VI collagen), complement components (e.g., C1q, C3, C3a, C3b, C4, C5, C6, C7, C8, C9), cytochrome C, cytochrome P450 2D6, cytokeratins, decorin, dermatan sulfate, DNA (e.g., double stranded DNA, single stranded DNA), DNA topoisomerase I, elastin, Epstein-Barr nuclear antigen 1 (EBNA1), elastin, entaktin, extractable nuclear antigens (Ro, La, Sm, RNP, Scl-70, Jo1), Factor I, Factor P, Factor B, Factor D, Factor H, Factor X, fibrinogen (e.g., fibrinogen IV, fibrinogen S), fibronectin, formiminotransferase cyclodeaminase (LC-1), gliadin and amidated gliadin peptides (DGPs), gp210 nuclear envelope protein, GP2 (major zymogen granule membrane glycoprotein), glycoprotein gpIIb/IIIa, glial fibrillary acidic protein (GFAP), glycated albumin, glyceraldehyde 3-phosphate dehydrogenase (GAPDH), haptoglobin A2, heat shock proteins (e.g., Hsp60, HSP70), hemocyanin, heparin, histones (e.g., histones H1, H2A, H2B, H3, H4), histidyl-tRNA synthetase (Jo-1), hyaluronidase, immunoglobulins, insulin, insulin receptor, integrins (e.g., integrins $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_L\beta_2$, $\alpha_M\beta_2$, $\alpha_{IIb}\beta_3$, $\alpha_V\beta_1$, $\alpha_V\beta_3$, $\alpha_V\beta_5$, $\alpha_V\beta_6$, $\alpha_V\beta_8$, $\alpha_6\beta_3$, $\alpha_1\beta_1$), interstitial retinol-binding protein 3, intrinsic factor, Ku (p70/p80), lactate dehydrogenase, laminin, liver cytosol antigen type 1 (LC1), liver/kidney microsomal antigen 1 (LKM1), lysozyme, melanoma differentiation-associated protein 5 (MDA5), Mi-2 (chromodomain helicase DNA binding protein 4), mitochondrial proteins (e.g., M1, M2, M3, M4, M5, M6, M7, M8, M9, BCOADC-E2, OGDC-E2, PDC-E2), muscarinic receptors, myelin-associated glycoprotein, myosin, myelin basic protein, myelin oligodendrocyte glycoprotein, myeloperoxidase (MPO), rheumatoid factor (IgM anti-IgG), neuron-specific enolase, nicotinic acetylcholine receptor α chain, nucleolin, nucleoporin (e.g., Nup62), nucleosome antigen, PM/Scl100, PM/Scl 75, pancreatic β-cell antigen, pepsinogen, peroxiredoxin 1, phosphoglucose isomerase, phospholipids, phosphotidyl inositol, platelet derived growth factors, polymerase beta (POLB), potassium channel KIR4.1, proliferating cell nuclear antigen (PCNA), proteinase-3, proteolipid protein, proteoglycan, prothrombin, recoverin, rhodopsin, ribonuclease, ribonucleoproteins (e.g., Ro, La, snRNP, scRNP), ribosomes, ribosomal phosphoproteins (e.g., P0, P1, P2), RNA (double stranded RNA, single stranded RNA), Sm proteins (e.g., SmB, SmB', SmD1, SmD2, SmD3, SmF, SmG, SmN), Sp100 nuclear protein, SRP54 (signal recognition particle 54 kDa), selectin, smooth muscle proteins, sphinomyelin, streptococcal antigens, superoxide dismutase, synovial joint proteins, T1F1 gamma collagen, threonyl-tRNA synthetase (PL-7), tissue transglutaminase, thyroid peroxidase, thyroglobulin, thyroid stimulating hormone receptor, transferrin, triosephosphate isomerase, tubulin, tumor necrosis alpha, topoisomerase, U1-dnRNP 68/70 kDa, U1-snRNP A, U1-snRNP C, U-snRNP B/B', ubiquitin, vascular endothelial growth factor, vimentin, and vitronectin.

Also disclosed herein are quantitative methods for performing an automated diagnostic assay for detection of an infectious disease by detecting antibodies to the infectious agent in a serum sample from a subject for the diagnosis of an autoimmune disease.

Infectious agents include, but are not limited to bacteria, virus, viroids, prions, nemotodes (e.g., roundworms, pinworms), parasites (malaria, tapeworm), and fungi (e.g., yeast, ringworm). As used herein the terms "infectious agent," "pathogen", "pathogenic microorganism" and "microorganism" all refer to the infectious agents listed above.

Antigens from infectious agents can be any isolated protein, glycoprotein, nucleic acid, enzyme, lipid, liposaccharide, or combination thereof, from an infectious agent. Antigens can also include extracts or homogenized preparations from infectious agents which include a plurality of different antigenic moieties.

In order to determine if a sample contains autoimmune antibodies to self antigens (autoantigens), or antibodies to an infectious agent, fluorescently labeled paramagnetic microparticles (e.g., fluo-beads) are bound to the autoantigen or infectious disease antigen according to methods disclosed herein to form a capture reagent. A sample of the cuvette is obtained prior to washing for a fluorescent reading to determination of the starting number of magnetic beads in the reaction cuvette.

After undergoing a washing process, the patient sample, and optionally a diluent if needed, is added to the particles in the cuvettes and incubated. This results in the capture of specific analyte molecules (antibodies) in the patient's blood sample. Another washing process is then performed to remove any excess or unbound sample, and then a luminescent label and a conjugate is added to the cuvette. When added to the cuvette, it can be expected that some portion of the conjugate will bind to the capture reagent/sample complex on the paramagnetic particles after an incubation period. The particles then undergo another wash process to remove any unbound conjugate, and then the substrate is added to the cuvette and incubated for a short period of time to allow the chemiluminescent glow reaction to reach equilibrium.

After equilibrium is reached, luminescence and fluorescence readings of the sample are taken and the levels of antibodies to the antigen are determined as disclosed herein.

Advantages and improvements of the processes, methods of the present disclosure are demonstrated in the following examples. These examples are illustrative only and are not intended to limit or preclude other embodiments of the present disclosure.

Example 1

Biotinylation of Anti-Human Ig or Antigen Extracts

Two microliters of NHS-PEG12-Biotin (Pierce) 250 mM in DMSO is added to 1 mL of affinity purified anti-human Ig (e.g., IgE, IgG, IgA, IgM) 5.0 mg/mL in phosphate buffered saline (PBS). Or, 1.6 µL of NHS-PEG12-Biotin (Pierce) 250 mM in DMSO is added to 1 mL of antigen extracts 1.0 mg/mL in PBS.

The reagent solution is mixed and placed on ice for 2 hours. Free biotin reagent is separated from the biotinylated antibody by dialysis against two changes of PBS (volume ratio of antibody to buffer—1:100) at 2-8° C. for 4 hours and overnight.

Example 2

Preparation of Fluo-Bead

Five microliters of Biotin-Fluo (Alexa Fluor 594 Biocytin, Sodium Salt, Life Technologies) 1 mM in ddH$_2$O is added into 45 mL of PBSTHP Buffer (10 mM sodium phosphate, pH 7.4, 0.9% (w/v) NaCl, 0.05% (v/v) Tween-20, 10 mg/mL HSA, 1% (v/v) ProClin 950). Mix well.

Five milliliters of SA-Speed Bead (Sera-mag Speedbeads Streptavidin-Coated Magnetic Particles, Thermo) 10 mg/mL is added into the Biotin-Fluo solution and mixed well.

Example 3

Assay for Specific Immunoglobulin Levels to Antigens

Ten microliters Fluo-Bead (Fluorescence labeled paramagnetic microparticles) at bead concentration 1 mg/mL is dispensed into the reaction cuvette; 40 µL of biotin-antigen (e.g., infectious disease antigen, autoantigen, etc) or biotin-anti-Ig antibody, is dispensed and mixed into the Fluo-Bead, and incubated for 1-10 min at 37° C. After washing, antigen- or anti-Ig-coated beads are resuspended in 40 µL of reaction buffer. Serum samples obtained from appropriate individuals are assayed against the antigens. A 10 µL sample was added to 40 µL of suspended antigen-coated beads in reaction cuvette. For the six point standard curve, 10 µL of serum standards (secondary standards calibrated against a WHO Ig Standard) are each added to 40 µL of anti-Ig-coated beads in a reaction cuvette. While various different labeled anti-Ig conjugates can be utilized in accordance with the present teachings, in accordance with certain teachings, the following anti-Ig conjugates are utilized: for assays: anti-IgE-HRP; anti-IgA-HRP, anti-IgG-HRP, anti-IgM-HRP, anti-ECP-HRP, and anti-tryptase-HRP. Moreover, as used herein, each conjugate has an optimized HRP incorporation ratio for use in the chemistry. In accordance with certain aspects of the present teachings, the range of HRP incorporation ratio used for the listed conjugates is between about 1.2 and about 5.4. In addition, the present teachings also contemplate the incorporation of other types of conjugate-reporter systems including, but not limited to: alkaline phosphatase conjugate and b-galactosidase conjugate.

The solutions are mixed and incubated for 40 min at 37° C. After washing, beads are resuspended in 50 µL of anti-human IgE-HRP conjugate, and incubated at 37° C. for 30 min. 50 µL of PS-ATTO® (LUMIGEN®) is added into each cuvette and the beads resuspended. The bead suspension is transferred into a pipette tip and read in the optic box for both fluorescence and luminescence signal. The standard curve was determined using a four parameter logistic function equation and levels of specific Ig to antigens interpolated from the standard curve.

A list of illustrative reagents and components that may be used in accordance with the present teachings include, but are not necessarily limited to: Bead: Fluo-Bead (SA-Speed Bead, Atto 590 labeled), 1 mg/mL; Capture Reagent Diluent: IgE:10 mM sodium phosphate, pH 7.4, 0.9% (w/v) NaCl, 0.05% Tween-20, 1% (w/v) human serum albumin, 1% (v/v) ProClin 950, up to 5% (v/v) glycerol; ANA: 10 mM sodium phosphate, pH 7.4, 0.9% (w/v) NaCl, 0.05% Tween-20, 1% (w/v) bovine serum albumin, 1% Protease inhibitor cocktail, 0.1 mM DTT, 1% (v/v) ProClin 950, 25% (up to 30%) (v/v) glycerol; Wash Buffer Concentrate (5x): 50 mM sodium phosphate, pH 7.4, 4.5% (w/v) NaCl, 0.05% Tween-20, 0.05% (v/v) ProClin 950, 0.02% (v/v) Antifoam-C v/v; Reagent Diluent (Reaction Diluent & Sample Diluent) IgE—10 mM sodium phosphate, pH 7.4, 500 mM NaCl, 0.02% Tween-20, 1% (w/v) human serum albumin, 1% (v/v) human IgG, 1% (v/v) ProClin 950, 0.005% Antifoam-B v/v, 2% (w/v) PEG 6,000; ANA—10 mM sodium phosphate, pH 7.4, 500 mM NaCl, 0.02% Tween-20, 25% (w/v) human serum albumin, 1% (v/v) ProClin 950; Calibrator & Control: Calibrator: Patient sample diluted into Sample Diluent;

Control: Patient Sample pool; Conjugate: Conjugate Diluent: 50 mM sodium phosphate, pH 6.7, 150 mM NaCl, 0.05% Tween-20, 1% BSA, 5% (w/v) PEG 6,000, 1% (v/v) ProClin 950; IgE:100 ng/mL anti-IgE-HRP, 100 µg/mL apo-HRP, in diluent, 0.015% Antifoam-B v/v; and Substrate: PS-ATTO® A & B, 0.01% Antifoam-B v/v.

Example 4

Assay for Specific Immunoglobulin Levels to Autoantigens

Ten microliters Fluo-Bead (Fluorescence labeled paramagnetic microparticles) at bead concentration 1 mg/mL is dispensed into the reaction cuvette; 40 µL of biotin-antigen (e.g., myelin basic protein, collagen, insulin, etc) or biotin-anti-IgG antibody (or alternatively, anti-IgM or anti-IgA), is dispensed and mixed into the Fluo-Bead, and incubated for 1-10 min at 37° C. A sample of the labeled Fluo-Bead is obtained to determine the starting number of beads. After washing, antigen- or anti-IgG-coated beads are resuspended in 40 µL of reaction buffer. Serum samples obtained from individuals are assayed against antigens. A 10 µL sample is added to 40 µL of suspended antigen-coated beads in reaction cuvette. For the six point standard curve, 10 µL of serum standards (secondary standards calibrated against the WHO IgG Standard) are each added to 40 µL of anti-IgG-coated beads in a reaction cuvette.

The solutions are mixed and incubated for 40 min at 37° C. After washing, beads are resuspended in 50 µL of anti-human IgG-HRP conjugate, and incubated at 37° C. for 30 min. 50 µL of PS-ATTO® (LUMIGEN®) is added into each cuvette and the beads resuspended. The bead suspension is transferred into a pipette tip and read in the optic box for both fluorescence and luminescence signal. The standard curve is determined using a four parameter logistic function equation and levels of specific IgG to the autoantigens interpolated from the standard curve.

Example 5

Assay for Specific IgG Levels to Infectious Agent Antigens

Ten microliters Fluo-Bead (Fluorescence labeled paramagnetic microparticles) at bead concentration 1 mg/mL is dispensed into the reaction cuvette; 40 µL of biotin-antigen (from e.g., human immunodeficiency virus, Ebola virus, *Mycobacterium tuberculosis*, etc) or biotin-anti-IgG antibody (or alternatively, anti-IgM or anti-IgA), is dispensed and mixed into the Fluo-Bead, and incubated for 1-10 min at 37° C. A sample of the labeled Fluo-Bead is obtained to determine the starting number of beads. After washing, antigen- or anti-IgG-coated beads are resuspended in 40 µL of reaction buffer. Serum samples obtained from individuals are assayed against antigens. A 10 µL sample is added to 40 µL of suspended antigen-coated beads in reaction cuvette. For the six point standard curve, 10 µL of serum standards (secondary standards calibrated against the WHO IgG Standard) are each added to 40 µL of anti-IgG-coated beads in a reaction cuvette.

The solutions are mixed and incubated for 40 min at 37° C. After washing, beads are resuspended in 50 µL of anti-human IgG-HRP conjugate, and incubated at 37° C. for 30 min. 50 µL of PS-ATTO® (LUMIGEN®) is added into each cuvette and the beads resuspended. The bead suspension is transferred into a pipette tip and read in the optic box for both fluorescence and luminescence signal. The standard curve is determined using a four parameter logistic function equation and levels of specific IgG to the infectious agent antigens interpolated from the standard curve.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A quantitative method for performing an automated diagnostic assay for an autoimmune disease comprising:
    dispensing a quantity of streptavidin-conjugated universal fluorescent-labeled magnetic microparticles into a reaction cuvette within a reaction rotor of an immunoanalyzer instrument using a first pipettor;
    measuring a first fluorescent signal associated with the quantity of streptavidin-conjugated universal fluorescent-labeled magnetic microparticles through an optics pipette;
    selecting a capture reagent suitable for performing the diagnostic assay, wherein the capture reagent is a biotinylated autoantigen;
    dispensing the capture reagent into the reaction cuvette using the first pipettor;
    incubating the capture reagent with the quantity of streptavidin-conjugated universal fluorescent-labeled magnetic microparticles to form a solid phase complex in the reaction cuvette;
    washing the solid phase complex to remove excess capture reagent;
    dispensing a serum sample into the reaction cuvette using a second pipettor;
    incubating the solid phase complex with the serum sample to form an immune complex;
    washing the immune complex to remove any unbound sample;
    dispensing a conjugate into the reaction cuvette using a third pipettor;
    incubating the immune complex with the conjugate to create an immune-conjugate complex;
    washing the immune-conjugate complex to remove any unbound conjugate;
    introducing a substrate capable of generating a quantifiable response using the third pipettor;
    transferring the substrate and immune-conjugate complex from the reaction rotor to an optics box using the optics pipette by aspirating the substrate and immune-conjugate complex from the reaction cuvette into the optics pipette;
    measuring a second fluorescent signal associated with the transferred material through the optics pipette and comparing the second fluorescent signal with the first fluorescent signal to obtain a bead retention value;
    measuring a chemiluminescent signal associated with the transferred material;
    determining the response generated from the substrate, and
    comparing a generated bead retention adjusted relative light unit signal to a calibration curve relative light unit signal; wherein one or more of the washing steps include washing the solid phase, immune, and/or immune-conjugate complexes by magnetically sequestering the solid phase, immune, and/or immune-conjugate complexes being washed within a confined area of the reaction cuvette; wherein incubating the capture reagent with the streptavidin conjugated universal fluorescent-labeled magnetic microparticles includes incubating a capture reagent that is retained in a suspension by a reaction diluent including at least about 25% human serum albumin (HSA); wherein incubating the immune complex with the conjugate comprises incubating the immune complex that is retained in a suspension by a conjugate diluent including no more than about 5% polyethylene glycol; and wherein horseradish peroxidase (HRP) is used as an indirect label when washing the immune complex to remove unbound sample.

2. The method of claim 1, wherein the step of incubating the solid phase complex with the serum sample comprises binding an autoimmune-specific human immunoglobulin G (IgG), an autoimmune-specific human immunoglobulin M (IgM) or an autoimmune-specific human immunoglobulin A (IgA) present in the serum sample to the capture reagent.

3. The method of claim 1, wherein the autoantigen is aggrecan, alanyl-tRNA syntetase (PL-12), alpha beta crystallin, alpha fodrin (Sptan 1), alpha-actinin, α1 antichymotrypsin, α1 antitripsin, α1 microglobulin, alsolase, aminoacyl-tRNA synthetase, an amyloid, an annexin, an apolipoprotein, aquaporin, bactericidal/permeability-increasing protein (BPI), β-globin precursor BP1, β-actin, β-lactoglobulin A, β2-glycoprotein I, β2-microglobulin, a blood group antigen, C reactive protein (CRP), calmodulin, calreticulin, cardiolipin, catalase, cathepsin B, a centromere protein, chondroitin sulfate, chromatin, collagen, a complement component, cytochrome C, cytochrome P450 2D6, cytokeratins, decorin, dermatan sulfate, DNA, DNA topoisomerase I, elastin, Epstein-Barr nuclear antigen 1 (EBNA1), elastin, entaktin, an extractable nuclear antigen, Factor I, Factor P, Factor B, Factor D, Factor H, Factor X, fibrinogen, fibronectin, formiminotransferase cyclodeaminase (LC-1), gliadin and amidated gliadin peptides (DGPs), gp210 nuclear envelope protein, GP2 (major zymogen granule membrane glycoprotein), glycoprotein gpIIb/IIIa, glial fibrillary acidic protein (GFAP), glycated albumin, glyceraldehyde 3-phosphate dehydrogenase (GAPDH), haptoglobin A2, heat shock proteins, hemocyanin, heparin, a histone, histidyl-tRNA synthetase (Jo-1), hyaluronidase, immunoglobulins, insulin, insulin receptor, an integrin, interstitial retinol-binding protein 3, intrinsic factor, Ku (p70/p80), lactate dehydrogenase, laminin, liver cytosol antigen type 1 (LC1), liver/kidney microsomal antigen 1 (LKM1), lysozyme, melanoma differentiation-associated protein 5 (MDA5), Mi-2 (chromodomain helicase DNA binding protein 4), a mitochondrial protein, muscarinic receptors, myelin-associated glycoprotein, myosin, myelin basic protein, myelin oligodendrocyte glycoprotein, myeloperoxidase (MPO), rheumatoid factor (IgM anti-IgG), neuron-specific enolase, nicotinic acetylcholine receptor α chain, nucleolin, a nucleoporin, nucleosome antigen, PM/Scl100, PM/Scl 75, pancreatic β-cell antigen, pepsinogen, peroxiredoxin 1, phosphoglucose isomerase, phospholipids, phosphotidyl inositol, platelet derived growth factors, polymerase beta (POLB), potassium channel KIR4.1, proliferating cell nuclear antigen (PCNA), proteinase-3, proteolipid protein, proteoglycan, prothrombin, recoverin, rhodopsin, ribonuclease, a ribonucleoprotein, ribosomes, a ribosomal phosphoprotein, RNA, an Sm protein, Sp100 nuclear protein, SRP54 (signal recognition particle 54 kDa), selectin, smooth muscle proteins, sphinomyelin, streptococcal antigens, superoxide dismutase, synovial joint proteins, T1F1 gamma collagen, threonyl-tRNA synthetase (PL-7), tissue transglutaminase, thyroid peroxidase, thyroglobulin, thyroid stimulating hormone receptor, transferrin, triosephosphate isomerase, tubulin, tumor necrosis alpha, topoisomerase, U1-dnRNP 68/70 kDa, U1-snRNP A, U1-snRNP C, U-snRNP B/B', ubiquitin, vascular endothelial growth factor, vimentin, or vitronectin.

4. The method of claim 1, further comprising entering the fluorescence and luminescence measurements into an algorithm to generate the bead retention adjusted relative light unit signal.

5. The method of claim 3, wherein the autoantigen is amyloid beta, amyloid P, annexin II, annexin V, apolipoproteins ApoB, apolipoproteins ApoE, apolipoproteins ApoE4, apolipoproteins ApoJ, aquaporin AQP1, aquaporin AQP2, aquaporin AQP3, aquaporin AQP4, Rh blood group antigens, I blood group antigens, ABO blood group antigens, CENP-A, CENP-B, collagen type I, collagen type II, collagen type III, collagen type IV, collagen type V, collagen type VI, complement components C1q, complement components C3, complement components C3a, complement components C3b, complement components C4, complement components C5, complement components C6, complement components C7, complement components C8, complement components C9, double stranded DNA, single stranded DNA, extractable nuclear antigen Ro, extractable nuclear antigen La, extractable nuclear antigen Sm, extractable nuclear antigen RNP, extractable nuclear antigen Scl-70, extractable nuclear antigen Jo1, fibrinogen IV, fibrinogen S, Hsp60, HSP70, histone H1, histone H2A, histone H2B, histone H3, histone H4, integrin α1β1, integrin α2β1, integrin α3β1, integrin α4β1, integrin α5β1, integrin α6β1, integrin α7β1, integrin αLβ2, integrin αMβ2, integrin αIIbβ3, integrin αVβ1, integrin αVβ3, integrin αVβ5, integrin αVβ6, integrin αVβ8, integrin α6β3, integrin α1β1, Ku p70/p80, mitochondrial protein M1, mitochondrial protein M2, mitochondrial protein M3, mitochondrial protein M4, mitochondrial protein M5, mitochondrial protein M6, mitochondrial protein M7, mitochondrial protein M8, mitochondrial protein M9, mitochondrial protein BCOADC-E2, mitochondrial protein OGDC-E2, mitochondrial protein PDC-E2, Nup62, rheumatoid factor IgM anti-IgG, ribonucleoprotein Ro, ribonucleoprotein La, ribonucleoprotein snRNP, ribonucleoprotein scRNP, ribosomal phosphoprotein P0, ribosomal phosphoprotein P1, ribosomal phosphoprotein P2, double stranded RNA, single stranded RNA, Sm protein SmB, Sm protein SmB', Sm protein SmD1, Sm protein SmD2, Sm protein SmD3, Sm protein SmF, Sm protein SmG, or Sm protein SmN.

* * * * *